US009615790B2

(12) United States Patent
Caprio et al.

(10) Patent No.: US 9,615,790 B2
(45) Date of Patent: Apr. 11, 2017

(54) SENSOR DEVICE WITH FLEXIBLE JOINTS (75) Inventors: Matthew Caprio, Seattle, WA (US);
Vanessa Beasley, Clayton, NC (US);
Gerald J. McMorrow, Redmond, WA (US); Andrew Clay, Everett, WA (US);
Jeffrey William Ladwig, Seattle, WA (US)

(73) Assignee: Verathon Inc., Bothell, WA (US)

( * ) Notice: Subject to any disclaimer, the term of this patent is extended or adjusted under 35 U.S.C. 154(b) by 0 days.

(21) Appl. No.: 13/183,262

(22) Filed: Jul. 14, 2011

(65) Prior Publication Data

US 2013/0018251 A1  Jan. 17, 2013

(51) Int. Cl.
*A61B 5/0408* (2006.01)
*A61B 5/00* (2006.01)

(52) U.S. Cl.
CPC ........ *A61B 5/6805* (2013.01); *A61B 5/04085* (2013.01); *A61B 5/04087* (2013.01); *A61B 5/6823* (2013.01); *A61B 5/6832* (2013.01); *A61B 2562/0209* (2013.01); *A61B 2562/04* (2013.01); *Y10T 29/49128* (2015.01)

(58) Field of Classification Search
CPC ... A61B 5/0245; A61B 5/0255; A61B 5/0402; A61B 5/0408; A61B 5/04085; A61B 5/04087; A61B 5/6801; A61B 5/6802; A61B 5/6804; A61B 5/6805; A61B 5/6823; A61B 5/6835; A61B 5/6832
USPC .......................... 600/382, 389, 391–393, 509
See application file for complete search history.

(56) References Cited

U.S. PATENT DOCUMENTS

| 4,763,660 | A  |   | 8/1988  | Kroll et al.         |         |
|-----------|----|---|---------|----------------------|---------|
| 5,184,620 | A  | * | 2/1993  | Cudahy et al.        | 600/382 |
| 5,191,887 | A  |   | 3/1993  | Cartmell             |         |
| 5,341,806 | A  | * | 8/1994  | Gadsby et al.        | 600/393 |
| 5,353,793 | A  | * | 10/1994 | Bornn                | 600/386 |
| 5,713,842 | A  |   | 2/1998  | Kay                  |         |
| 5,868,671 | A  |   | 2/1999  | Mahoney              |         |
| 6,055,448 | A  | * | 4/2000  | Anderson et al.      | 600/372 |
| 6,115,638 | A  |   | 9/2000  | Groenke              |         |
| 6,141,575 | A  |   | 10/2000 | Price                |         |
| 6,301,493 | B1 |   | 10/2001 | Marro et al.         |         |
| 6,415,169 | B1 | * | 7/2002  | Kornrumpf et al.     | 600/382 |
| 6,553,247 | B1 | * | 4/2003  | Rytky                | 600/386 |
| 6,711,427 | B1 |   | 3/2004  | Ketelhohn            |         |
| 6,745,062 | B1 |   | 6/2004  | Finneran et al.      |         |
| 7,027,877 | B2 |   | 4/2006  | Dupelle et al.       |         |
| 7,173,437 | B2 |   | 2/2007  | Hervieux et al.      |         |
| 7,206,630 | B1 | * | 4/2007  | Tarler               | 600/509 |

(Continued)

FOREIGN PATENT DOCUMENTS

WO    2009/139911 A2    11/2009

*Primary Examiner* — Lee S Cohen
*Assistant Examiner* — Erin M Cardinal
(74) *Attorney, Agent, or Firm* — Snyder, Clark, Lesch & Chung, LLP (57) ABSTRACT

A sensor device for monitoring bioelectric data from a human body includes a flexible dielectric substrate, a plurality of sensors (electrodes) distributed on the substrate for sensing the bioelectric data, and an electrically conductive network distributed on the substrate connecting the sensors to a terminal portion of the substrate. Integrated flexible joints permit a certain amount of elasticity in and allow relative movement between at least two of the sensors when the sensor device is placed onto the human body.

7 Claims, 8 Drawing Sheets

(56) References Cited

U.S. PATENT DOCUMENTS

| | | | |
|---|---|---|---|
| 7,211,053 B2 | 5/2007 | Marmaropou | |
| 8,019,402 B1* | 9/2011 | Kryzpow et al. | 600/386 |
| 8,897,851 B2* | 11/2014 | Caprio et al. | 600/389 |
| 2002/0072682 A1* | 6/2002 | Hopman et al. | 600/509 |
| 2005/0251003 A1* | 11/2005 | Istvan et al. | 600/393 |
| 2007/0089800 A1* | 4/2007 | Sharma | D02G 3/441 139/388 |
| 2007/0155119 A1 | 7/2007 | Muemmler et al. | |
| 2007/0299471 A1* | 12/2007 | Takahashi | A61B 5/04085 607/2 |
| 2008/0154110 A1* | 6/2008 | Burnes et al. | 600/382 |
| 2008/0177168 A1* | 7/2008 | Callahan et al. | 600/382 |
| 2010/0101733 A1 | 4/2010 | Yu Chen et al. | |
| 2011/0015498 A1 | 1/2011 | Mestrovic et al. | |
| 2011/0275921 A1* | 11/2011 | Revishvili | A61B 5/04023 600/382 |
| 2012/0246795 A1* | 10/2012 | Scheffler | A41D 1/002 2/69 |
| 2012/0271141 A1* | 10/2012 | Davies et al. | 600/382 |
| 2013/0281814 A1* | 10/2013 | Tilt | A61B 5/04085 600/382 |

\* cited by examiner

SENSOR DEVICE WITH FLEXIBLE JOINTS

FIELD OF THE INVENTION

This invention relates generally to a sensor device for monitoring bioelectric data from a thoracic region of a human body and, more specifically, to a conformable sensor device that flexibly adapts to a contour of the thoracic region when placed in contact therewith.

BACKGROUND OF THE INVENTION

Conventional electrocardiogram (ECG) devices typically employ a twelve-lead system. ECG systems employing more than twelve leads are also known. The conventional twelve-lead systems typically use individual leads that are connected to a patient; whereas in systems using more than 12 leads, such as an 80 lead system, the electrodes are generally arranged as part of an electrode vest that is adhered to the patient. By way of example, one type of electrode vest is described in U.S. Pat. No. 6,055,448. Electrode vests are typically flat and somewhat flexible, but are prone to kinking and wrinkling when positioned on a pliable curved surface such as the human body. Moreover, the electrode vests include long finger-like sections that make them a bit unwieldy and difficult to place on the body without the sections sticking together or sticking to an unwanted portion of the body.

Figure 1A:
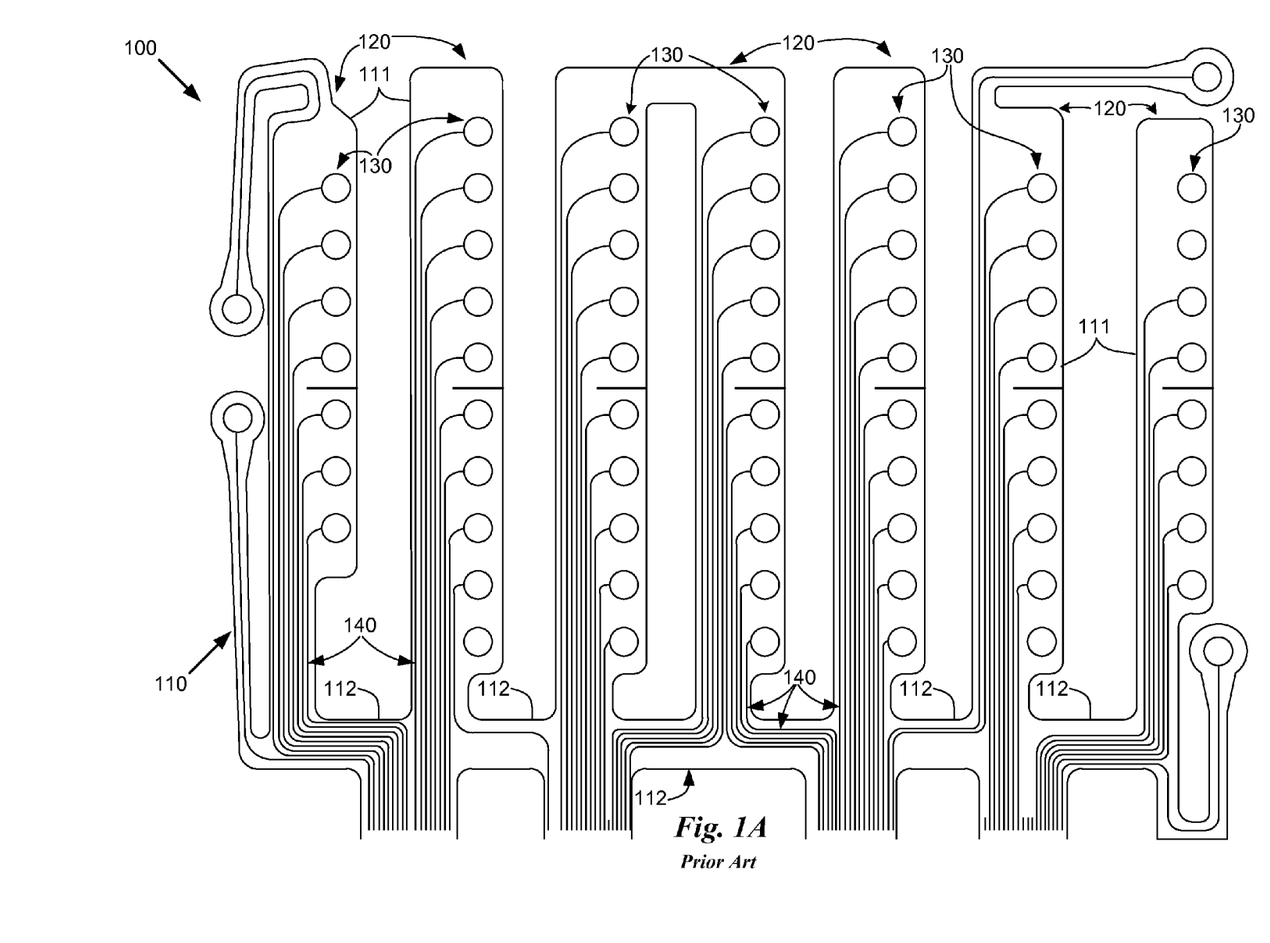
FIG. 1A is plan view of an anterior portion of a prior art sensor device in the form of a vest.
Figure 1B:
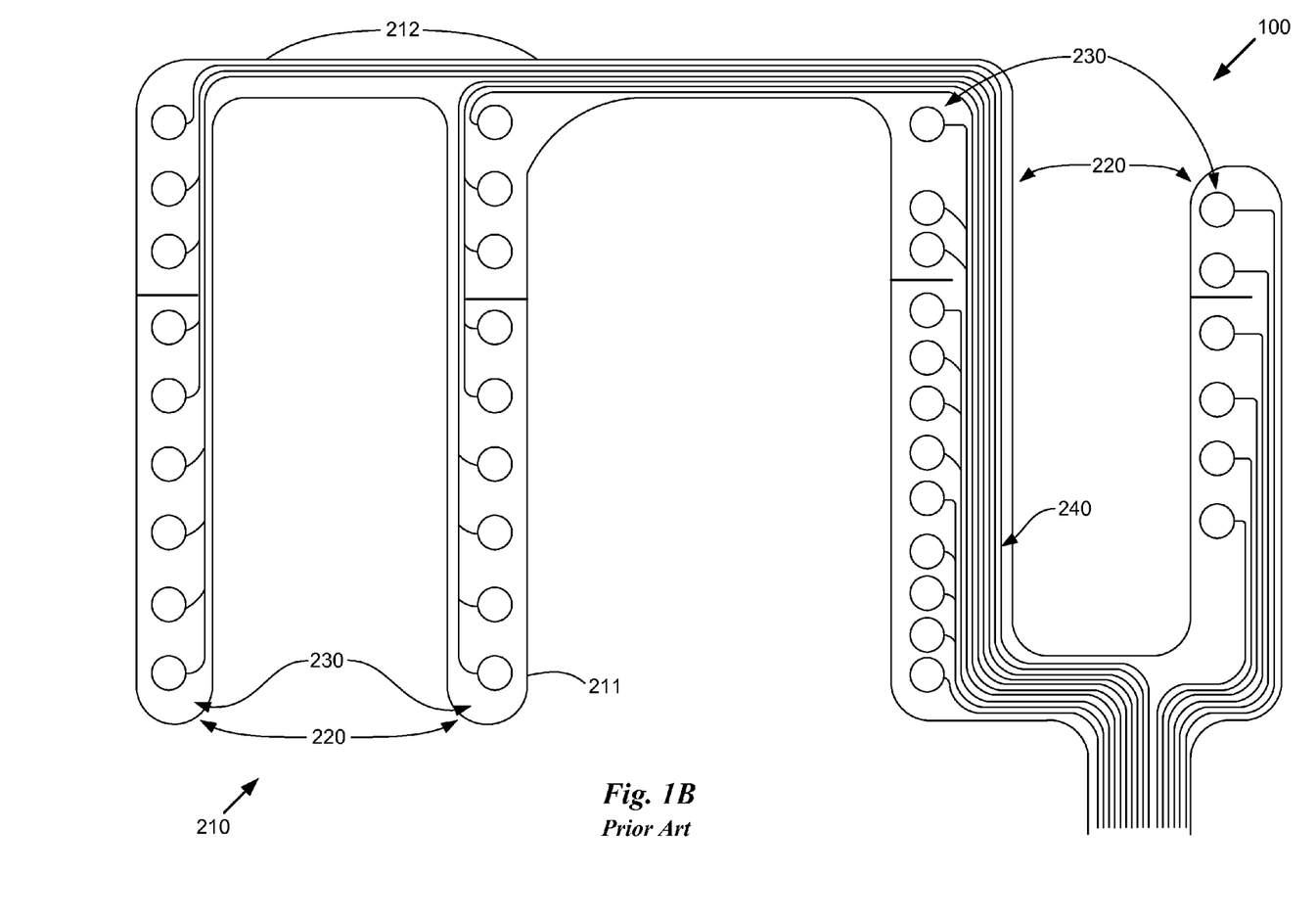
FIG. 1B is a plan view of a posterior portion of the prior art sensor device of FIG. 1A.

FIGS. 1A and 1B illustrate a prior art sensor device 100 in the form of a vest that may be applied to a human patient's torso for receiving bioelectric signals or delivering stimulating signals to a patient. Anterior portion 110 (FIG. 1A) is suitable for placing on the front of the patient's thoracic region and includes a flexible, dielectric substrate 111 having vertical, finger-like projections 120. Horizontal, common substrate portions 112 join the finger-like projections 120. A plurality of sensors or electrodes 130 are connected to a network of conductive traces 140 and are located on substrate 111. Bioelectric signals from the patient are detected by the sensors 130 and transmitted via traces 140 to a suitable medical device, such as an electrocardiogram (ECG) base unit (not shown).

FIG. 1B shows a posterior portion 210 of prior art device 100. Posterior portion 210 similarly includes flexible substrate 211 having vertical, finger-like projections 220. Horizontal, common substrate portions 212 join the finger-like projections 220. A plurality of sensors or electrodes 230 are connected to a network of conductive traces 240 and are located on substrate 211. Bioelectric signals from the patent are detected by the sensors 230 and transmitted via traces 240 to an ECG base unit or other suitable medical device (not shown).

Figure 2A:
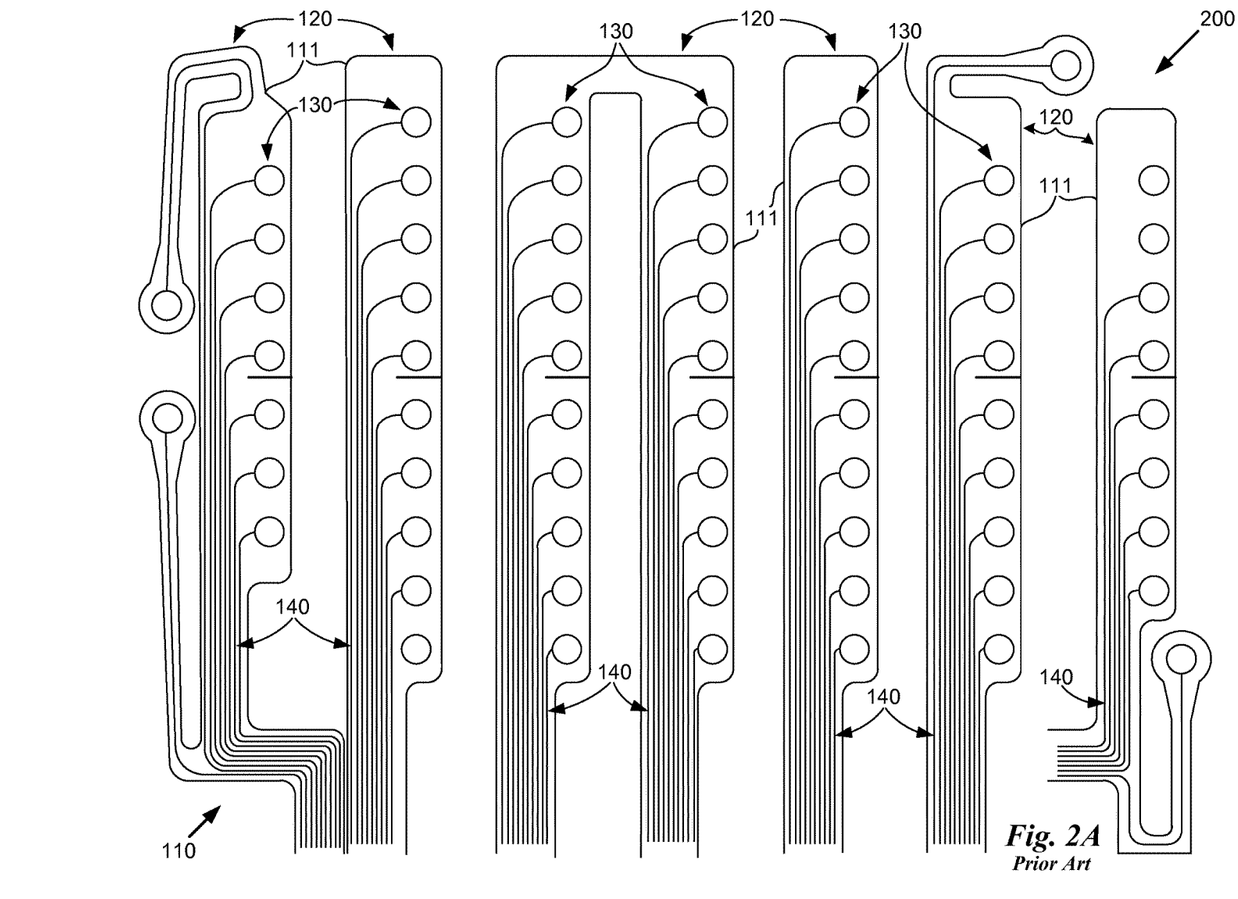
FIG. 2A is a plan view of an anterior portion of another embodiment of a prior art sensor device in the form of a vest.
Figure 2B:
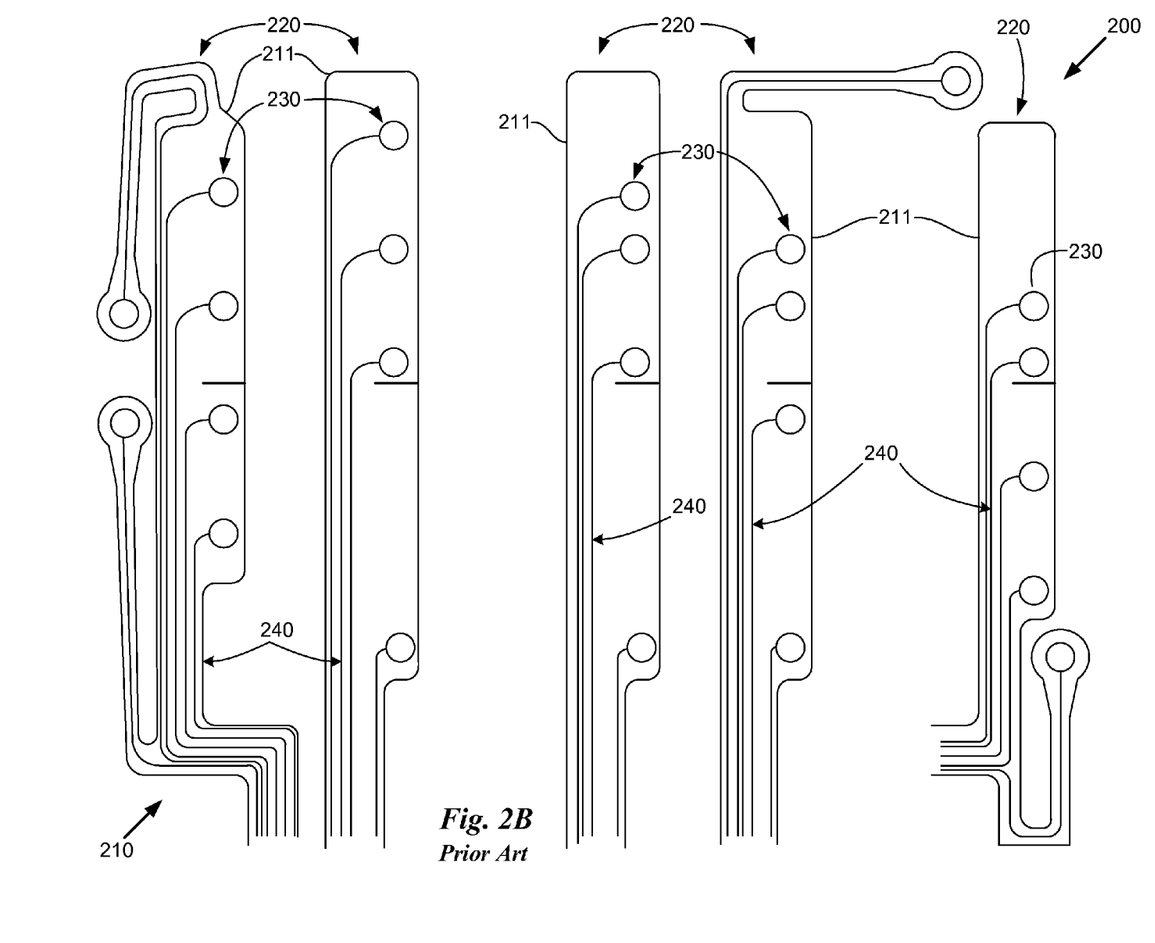
FIG. 2B is a plan view of a posterior portion of the prior art sensor device of FIG. 2A.

FIGS. 2A and 2B illustrate another embodiment of a prior art sensor device 200 also in the form of a vest. For purposes of clarity, similar elements in FIGS. 1A-1B and 2A-2B are identified with identical reference numbers. Absent from the embodiment of the anterior portion 110 (FIG. 2A) and posterior portion 210 (FIG. 2B) of prior art device 200 are the common substrate portions 112, 212 connecting finger-like projections 120, 220, the absence of which essentially lengthen the finger-like projections 120, 220.

As can be appreciated from the foregoing discussion of prior art sensor devices 100, 200 and as illustrated in FIGS. 1A-B, 2A-B, the flexible nature of substrate 111, 211 along with the long finger-like projections 120, 220 may make the sensor device 100, 200 difficult to handle and, as a result, difficult to properly and accurately place the electrodes 130, 230 on the patient's body. Further, the long vertical network of conductive traces may stiffen portions of the sensor device 100, 200 and cause the device 100, 200 to buckle or wrinkle when the patient moves, resulting in the electrodes 130, 230 becoming dislodged from the patient.

SUMMARY OF THE INVENTION

In accordance with an embodiment of the present invention, a sensor device for monitoring bioelectric data from a human body includes a flexible dielectric substrate, a plurality of sensors arranged on the substrate for sensing the bioelectric data, a terminal portion arranged on the substrate, a flexible, electrically conductive network arranged on the substrate and configured to provide electrical communication between the sensors and the terminal portion of the substrate, and a flexible joint integrated with the substrate that permits a desired amount of relative motion between at least two of the plurality of sensors when placing the substrate onto the human body.

In accordance with another example of the invention, a portion of a sensor device for monitoring bioelectric data from a human body includes a flexible, dielectric substrate, a plurality of sensors arranged on the substrate for sensing the bioelectric data, and a flexible joint coupled to the substrate, the flexible joint being configured to permit a desired amount of relative displacement between at least two of the plurality of sensors when the substrate is placed onto the human body.

In accordance with another example of the invention, a method of making a sensor vest for monitoring bioelectric data from a human body includes forming a flexible, dielectric substrate into a vest shape, arranging a plurality of sensors on the substrate for sensing the bioelectric data and coupling at least one flexible joint to the substrate, the flexible joint configured to permit a desired amount of relative displacement between at least two of the plurality of sensors when the substrate is placed onto the human body.

These and other examples of the invention will be described in further detail below.

BRIEF DESCRIPTION OF THE DRAWINGS

Preferred and alternative examples of the present invention are described in detail below with reference to the following drawings.

DETAILED DESCRIPTION OF THE PREFERRED EMBODIMENT

As previously discussed, prior art electrode vests are typically flat and while somewhat flexible, are prone to kinking and wrinkling when positioned on a pliable curved surface, such as the human body. Moreover, these electrode vests may include long finger-like sections that make them an unwieldy and difficult to place onto the body without the sections sticking together or sticking to an unwanted portion of the body. Accordingly, there is a need for a sensor device or vest that is easy to use and which better conforms to the contours of the patient's anatomy.

Figure 3A:
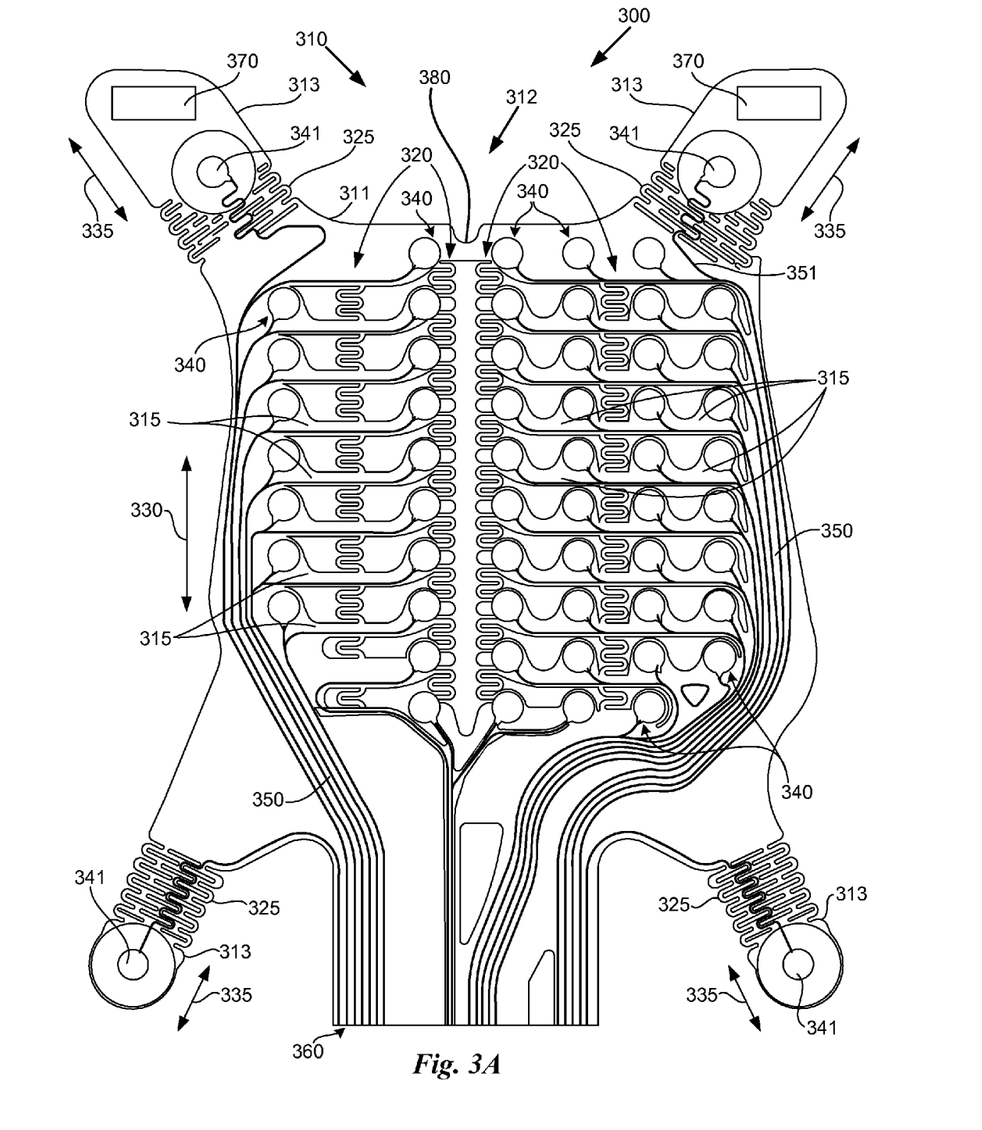
FIG. 3A is a plan view of an anterior portion of an embodiment of a sensor device in accordance with the present invention.
Figure 3B:
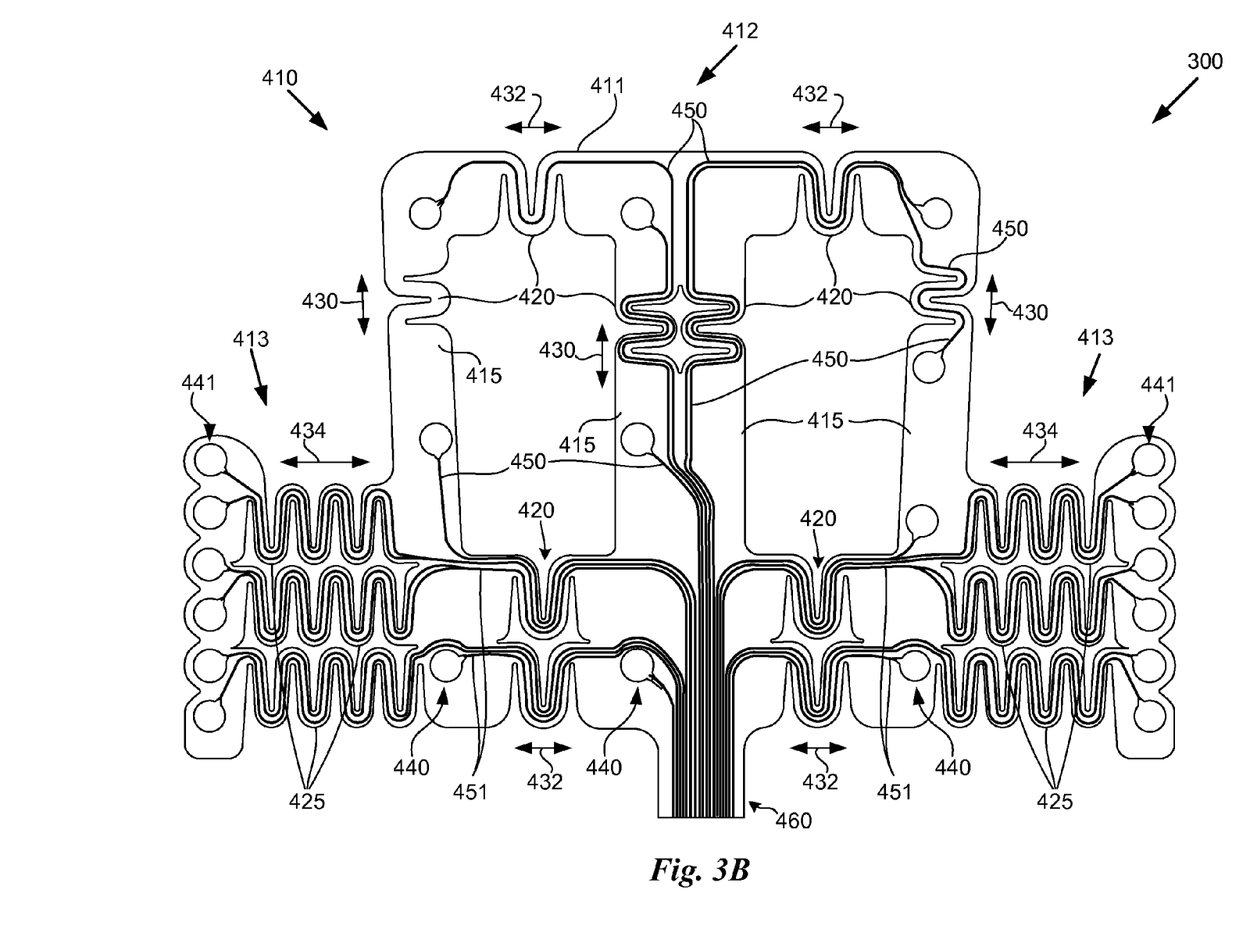
FIG. 3B is a plan view of a posterior portion of the sensor device of FIG. 3B.

FIGS. 3A and 3B illustrate a sensor vest 300 according to an embodiment of the present invention suitable for sensing bioelectric data from the patient or supplying stimulus signals to the patient. Sensor vest 300 includes an anterior portion 310 (FIG. 3A) that is suitable for applying to a patient's front thoracic region and a posterior portion 410 (FIG. 3B) suitable for applying to the patient's back and side (lateral) thoracic regions.

Referring to FIG. 3A, anterior portion 310 includes a flexible, dielectric substrate 311 having a central portion 312 and extensions 313 extending from the central portion 312. Substrate 311 (and substrate 411, which is discussed below and illustrated in FIG. 3B) may be made from materials such as, but not limited to, a MYLAR® polyester film, which in turn may be produced with conventional manufacturing processes to produce a flexible, strong and durable vest 300 having a desired dielectric strength, moisture resistance and physical durability.

Referring now to the central portion 312 of FIG. 3A, flexible joints 320 may be integrated with the substrate 311 to allow relative movement between the sensors at least in the general direction illustrated by arrow 330. In an alternate embodiment, the flexible joints 320 may be separately attached to the substrate 311 at selected locations to obtain a desired amount of flexibility in the sensor vest 300 (FIG. 5C and discussed below). The flexible joints 320 may take the form of springs, corrugated members repeatedly folded onto themselves to operate like a spring, thin links or some other biasing device that permits relative motion between various portions of the sensor vest 300. Flexible joints 320 connect a plurality of electrode sections 315 of substrate 311, in which each electrode section 315 includes at least one sensor or electrode 340 and an electrical network of conductive traces 350 that permit electrical communication between the electrodes 340 and a terminal portion 360.

By stretching the central portion 312 in the direction of arrow 330, the electrodes 340 are displaced relative to each other in the general direction of arrow 330, which allows the sensor vest 300 to better conform to the contours of the patient's body, which in turn advantageously permits a more accurate placement of the electrodes 340 on the patient's body and accommodates patient motions.

Extensions 313 include flexible joints 325 that connect each extension 313 to the central portion 312. Each extension 313 includes a sensor or electrode 341 connected to terminal portion 360 by a conductive trace, or electrical network, 351 that passes along flexible joint 325. Flexible joints 325 permit movement of extensions 313 at least in the general direction indicated by adjacent arrows 335. The flexible joints 325 also allow the electrical traces 351 to move or stretch with extensions 313, further enhancing the ability of vest 300 to conform to the contours of the patient's body. Extensions 313 may include adhesive patches 370 that permit additional adherence to the patient. When the vest 300 is used for ECG applications, the extensions 313 may be stretched as needed to allow electrodes 341 to be placed on the patient' right and left arms (or shoulders) and legs (or lower abdomen), thereby functioning as RA, LA, RL and LL electrodes. Proper positioning of the vest 300 is further enhanced by positioning indicia 380.

Each of electrical traces 350, 351 are terminated at one end to electrodes 340, 341 and at the opposite end at terminal portion 360. A connector (not shown) may then be coupled to the terminal portion 360 in any number of conventional ways for connecting the vest 300 to a medical monitoring device (also not shown) for analyzing the bioelectric data from the patient. Likewise a connector may be coupled to the terminal portion 360 in any number of known ways for connecting the vest 300 to a medical sourcing device (not shown) for providing stimulus signals to the patient.

Turning to FIG. 3B, posterior portion 410 includes a flexible, dielectric substrate 411 having a central portion 412 and side extensions 413 extending from the left and right sides of central portion 412. Central portion 412 includes flexible joints 420 that may be integrated into the substrate to allow relative movement of portions of the substrate 411 at least in the general directions indicated by adjacent arrows 430, 432. Flexible joints 420 connect electrode sections 415 of substrate 411 having at least one electrode or sensor 440 and an electrical network of one or more conductive traces 450 connecting electrodes 440 to a terminal portion 460. Stretching the central portion 412 in the directions of arrows 430, 432 permits the displacement of electrodes 440 in the general directions of the arrows 430, 432, which allows greater conformability of vest 300, a more accurate placement of electrodes 440 on the posterior of the patient's thoracic region, and better accommodates patient motions.

The side extensions 413 include flexible joints 425 connecting each extension 413 to the central portion 412. Each side extension 413 includes at least one sensor or electrode 441 connected to the terminal portion 460 by a conductive trace, or electrical network, 451. The conductive traces 451 pass along flexible joints 425, which permit the side extensions 413 to be stretched in the general direction indicated by arrows 434 and to be placed on the patient's right and left (lateral) sides. Flexible joints 425 also allow relative movement of electrical traces 451 with side extensions 413, further enhancing the ability of vest 300 to conform to the contours of the patient's body.

Each of electrical traces 450, 451 are terminated at one end to a terminal portion 460 and at the opposite end to the electrodes 440, 441. A connector (not shown) may then be coupled to the terminal portion 460 in a manner similar to that described above with reference to anterior portion 310 (FIG. 3A).

As depicted in FIGS. 3A and 3B, flexible joints 320, 325, 420, 425 may be spring elements that are integrated with substrates 311, 411 to provide controllable, elasticity and self-limiting displacement of the vest 300 for better anatomical fit, while providing sufficient integrity for handling and manufacturing.

In accordance with one embodiment of the present invention, an 80-electrode vest 300 requires a network of electrical conductors in the form of conductive traces 350, 351, 450, 451 to carry ECG signals from their respective electrodes 340, 341, 440, 441 on the patient's torso to the terminal portions 360, 460 for connection to one or more electrical connectors (not shown). These conductive traces 350, 351, 450, 451 may be screen printed or formed on dielectric substrate 311, 411, by conventional methods. Such traces, for example, may be 0.020-0.035 inches wide with a film thickness of 0.0005 inches to provide an adequate conductive cross section to reliably and durably transmit bioelectric signals.

The networks of conductive traces 350, 450, 451 have been combined in FIGS. 3A and 3B for clarity and illustrative purposes only. In a preferred embodiment, each trace 350, 450, 451 continues discretely from a corresponding electrode 340, 341, 440, 441 to terminal portion 360, 460.

As shown in FIGS. 3A and 3B, the horizontal routing of traces 350, 351, 450, 451 and the arrangement of flexible joints 320, 325, 420, 425, allows the vest 300 to function as a flexible, stretchable and, therefore, conformable vest for use with human patients. Prior art vests routed the conductive traces primarily in nested vertical paths (see generally FIGS. 1A, 1B, 2A, 2B). These vertical trace bundles result in semi-rigid bands of material, which have a tendency to behave as beams which buckle when the patient bends or stretches, sometimes causing electrodes to detach from the patient's skin. On the other hand, the use of more predominate, horizontal routing of conductive traces and the integrated flexible joints allows the vest 300 to stretch and better conform to the patient's torso.

Electrodes 340, 341, 440, 441 may be adhered to the patient using conventional methods and materials, including conductive gels and adhesives. Such materials may be pre-applied to the electrodes by the vest manufacturer so that a medical technician need only expose the electrodes immediately prior to placing them on the patient. If the electrodes are not provided with a pre-applied gel, the user would need to add gel to the electrodes prior to placing them onto the patient.

Figure 4:
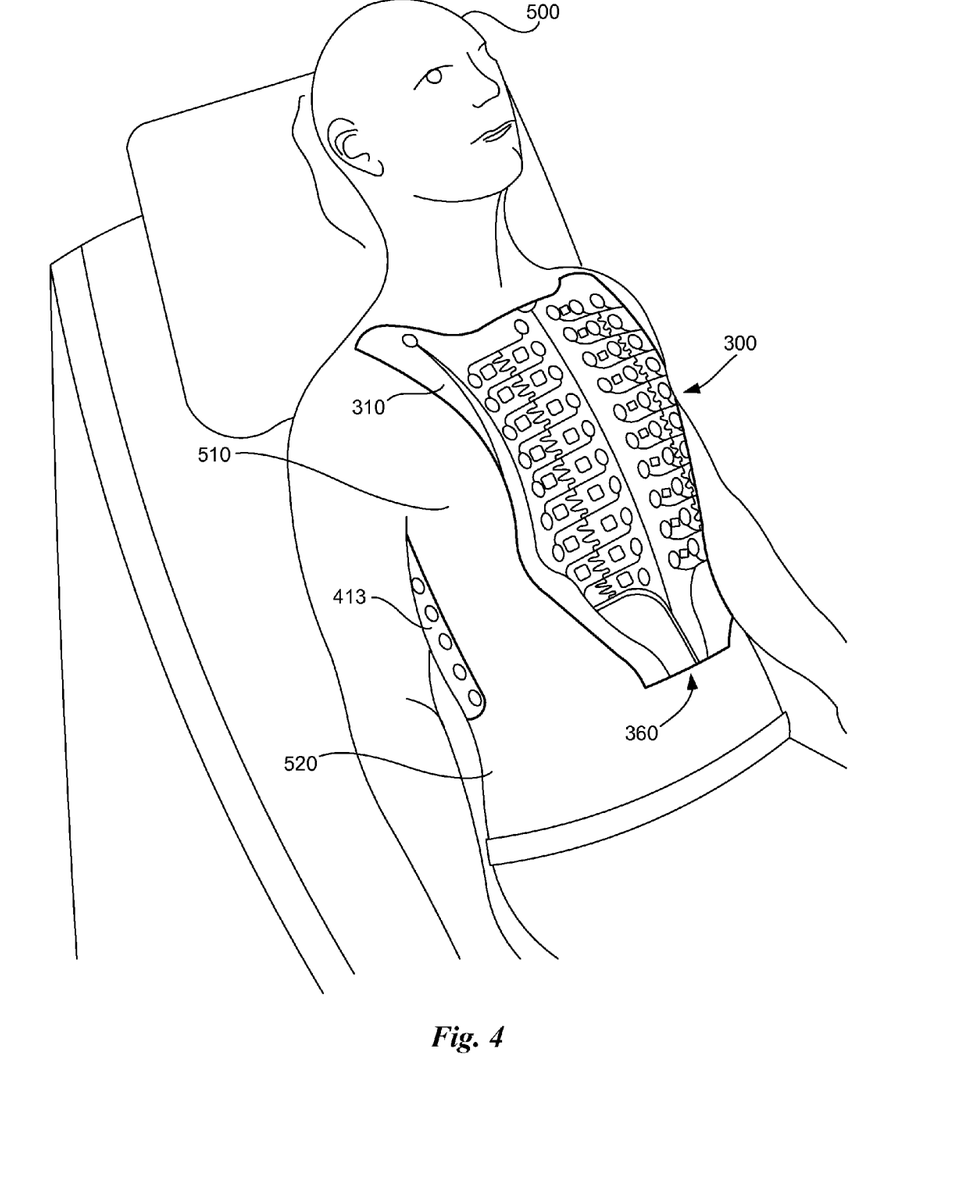
FIG. 4 is a perspective view of the sensor device of FIGS. 3A and 3B positioned on the body of a human patient; and, FIGS. 5A, 5B and 5C are schematic views of flexible joints according to alternative embodiments of the present invention.

FIG. 4 shows an embodiment of vest 300 placed on a human patient 500. The anterior portion 310 is shown on the front of the patient's torso 510 and a side extension 413 of the posterior portion (not shown but understood to be placed on the patient) is attached to the patient's right side 520 along the midaxillary line. The other side extension 413 is not shown but, likewise, is understood to be present on the patient 500. Terminal portion 360 is shown at the bottom of the anterior portion 310. Connectors, leads and monitoring/sourcing devices that are normally coupled to vest 300 are not shown for purposes of clarity.

Figure 5A:
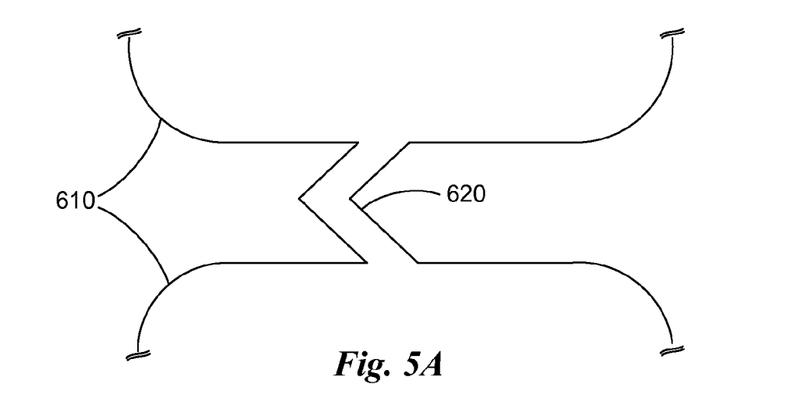
Figure 5B:
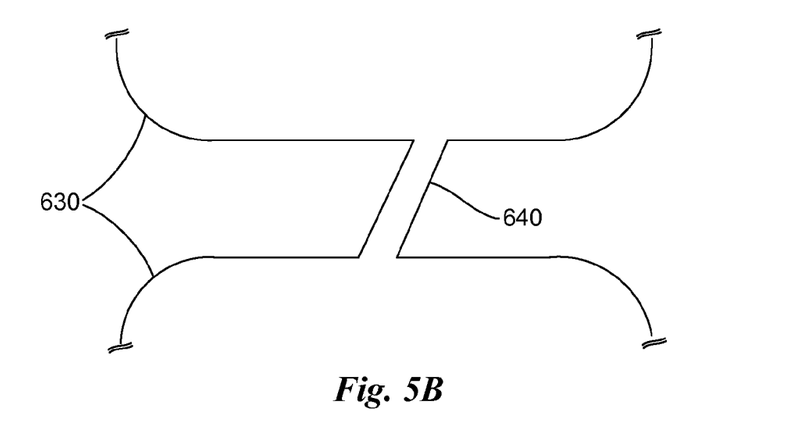
Figure 5C:
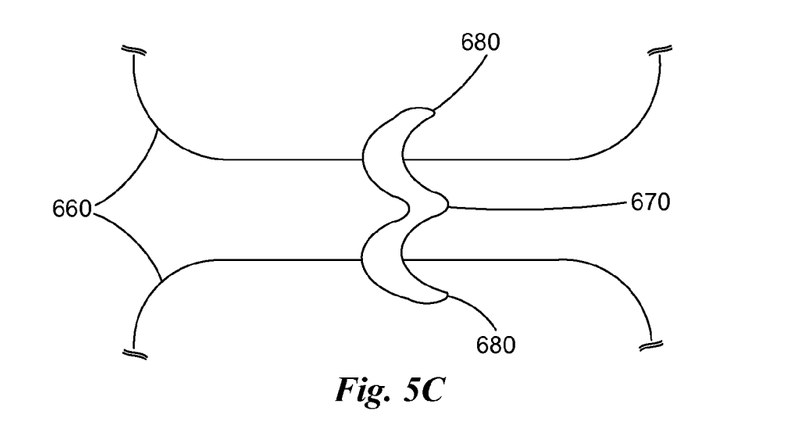

FIGS. 5A, 5B and 5C illustrate additional examples of flexible joints that are suitable for use in a vest according to alternate embodiments of the present invention. In FIG. 5A, portions of a vest substrate 610 are joined by a flexible joint 620 in the form of an angular member that is integrated with substrate portions 610. FIG. 5B shows substrate portions 630 coupled by a flexible joint 640 in the form of a thin, relatively straight and flexible member that is integrated with the substrate portions 630 and allows the joined portions of the substrate to move relative to one another. FIG. 5C illustrates yet another example of a flexible joint 670 in the form of a corrugated link connecting substrate portions 660. Unlike the previous examples discussed above, flexible joint 670 is not integrated with the substrate portions, but rather is affixed at ends 680 to the substrate by glue, ultrasonic welds or other conventional means for joining materials.

As previously discussed, conventional electrode vests used for ECG monitoring and other medical applications with human patients are generally unwieldy and difficult to apply to the patients and do not readily conform to the contours of the patient's body, causing electrodes to possibly become dislodged. The flexible joints and the orientation of conductive traces on the dielectric of an electrode vest in accordance with the present invention provides a vest that is easy to handle and conforms to the patient's body allowing electrodes to be readily placed and remain in place on the patient's body.

While the preferred embodiment of the invention has been illustrated and described, many changes can be made without departing from the spirit and scope of the invention. For example, the geometry of the flexible joints and the way in which they are attached or integrated with the substrate may be different than as depicted in the figures and described above. Likewise, the orientation of flexible joints may be more or less complex allowing the vest to be stretched in different directions. The vest may include fewer or more sensors than depicted in the figures and described above. Also, the vest may not have the appearance of a vest, but may have, for example, sleeves or leg portions, or a single piece design resembling a shirt. Further, the posterior and anterior portions may connect to one another by any known means, including hook and loop fasteners, zippers, buttons or via the material's inherent cling properties. Accordingly, the scope of the invention is not limited by the disclosure of the preferred embodiment. Instead, the invention should be determined entirely by reference to the claims that follow.

The embodiments of the invention in which an exclusive property or privilege is claimed are defined as follows:

1. A sensor device for monitoring bioelectric data from a human body, the sensor device comprising:
   a central portion of the sensor device having:
   a flexible, dielectric substrate having a substrate surface sized to substantially overlay a thoracic region of the human body, the substrate divisible into a plurality of electrode sections arranged laterally in at least three or more rows,
   at least two central portion sensors located within each electrode section, the central portion sensors operable for sensing the bioelectric data,
   a terminal portion arranged on the substrate,
   a flexible, electrically conductive network arranged on the substrate, the network configured to provide electrical communication between the central portion sensors and the terminal portion of the substrate, and
   a plurality of central portion flexible joints connecting adjacent rows of the electrode sections, the plurality of central portion flexible joints integrated with and formed in-plane with the substrate, the central portion flexible joints configured to provide expansion or contraction of the substrate coincident with the substrate surface while further permitting a desired amount of relative motion in a first direction between the central portion sensors when placing the substrate onto the human body; and
   an extension portion, distinct from the central portion and extending from the central portion, the extension portion having an extension portion flexible joint indirectly coupled to the central portion flexible joints, an extension portion sensor, and a conductive trace, wherein the extension portion sensor is locatable on or near a limb of the human body, wherein the extension portion flexible joint enables adjustment of the position of the extension portion sensor relative to the central portion in a second direction disposed at an angle with respect to the first direction, and wherein the conductive trace electronically couples the extension portion to the central portion.

2. The sensor device of claim 1, wherein a first portion of the substrate is biased relative to a second portion of the substrate by operation of one or more of the plurality of central portion flexible joints.

3. The sensor device of claim 1, wherein the substrate includes an anterior portion for contacting a front surface of the human body.

4. The sensor device of claim 1, wherein the substrate includes posterior portion for contacting a back surface of the human body.

5. The sensor device of claim 1, wherein one or more of the plurality of central portion flexible joints includes a spring.

6. A sensor device for monitoring bioelectric data from a human body, the sensor device comprising:
- a flexible, dielectric substrate including an anterior portion for contacting a front surface of the human body and a posterior portion for contacting a back surface of the human body;
- a plurality of sensors arranged on the substrate for sensing the bioelectric data;
- a terminal portion arranged on the substrate;
- a flexible, electrically conductive network arranged on the substrate, the network configured to provide electrical communication between the sensors and the terminal portion of the substrate; and
- a flexible joint integrated with the substrate, the flexible joint configured to permit a desired amount of relative motion in first and second directions among at least three of the plurality of sensors when placing the substrate onto the human body, the second direction being disposed at an angle with respect to the first direction.

7. A sensor device for monitoring bioelectric data from a human body, the sensor device comprising:
- a central portion of the sensor device having:
  - a flexible, dielectric substrate having a substrate surface sized to substantially overlay a thoracic region of the human body, the substrate divisible into a plurality of electrode sections,
  - at least one central portion sensor located within each electrode section, the central portion sensors operable for sensing the bioelectric data,
  - a terminal portion arranged on the substrate,
  - a flexible, electrically conductive network arranged on the substrate, the network configured to provide electrical communication between the central portion sensors and the terminal portion of the substrate, and
  - a plurality of central portion flexible joints connecting adjacent rows of the electrode sections, the plurality of central portion flexible joints integrated with and formed in-plane with the substrate, the central portion flexible joints configured to provide expansion or contraction of the substrate coincident with the substrate surface while further permitting a desired amount of relative motion in a first direction between the central portion sensors when placing the substrate onto the human body; and
- an extension portion, distinct from the central portion and extending from the central portion, the extension portion having an extension portion flexible joint indirectly coupled to the central portion flexible joints, an extension portion sensor, and a conductive trace, wherein the extension portion sensor is locatable on or near a limb of the human body, wherein the extension portion flexible joint enables adjustment of the position of the extension portion sensor relative to the central portion in a second direction different from the first direction, and wherein the conductive trace electronically couples the extension portion to the central portion.

* * * * *